United States Patent
Mistry et al.

(10) Patent No.: US 7,902,487 B2
(45) Date of Patent: Mar. 8, 2011

(54) SYSTEMS FOR REDUCING SLOW ROLL

(75) Inventors: Rajendra Mistry, Cincinnati, OH (US); Jason Obermeyer, West Chester, OH (US); Dennis Dixon, Cincinnati, OH (US)

(73) Assignee: Siemens Industry, Inc., Alpharetta, GA (US)

( * ) Notice: Subject to any disclaimer, the term of this patent is extended or adjusted under 35 U.S.C. 154(b) by 211 days.

(21) Appl. No.: 11/436,959

(22) Filed: May 17, 2006

(65) Prior Publication Data

US 2006/0288787 A1    Dec. 28, 2006

Related U.S. Application Data

(60) Provisional application No. 60/682,075, filed on May 18, 2005.

(51) Int. Cl.
  *H05B 6/10* (2006.01)
  *G01B 7/14* (2006.01)

(52) U.S. Cl. .................... 219/637; 219/494; 324/207.13

(58) Field of Classification Search .................. 219/637, 219/607, 608, 652, 643, 635, 654, 656, 672, 219/657, 659; 148/572, 330, 440, 239, 111, 148/224, 233, 319, 328; 266/129, 249, 259, 266/193, 197, 124; 29/421.1, 430; 74/422, 74/498; 324/207.13; 399/69
See application file for complete search history.

(56) References Cited

U.S. PATENT DOCUMENTS

| | | | |
|---|---|---|---|
| 5,034,588 A * | 7/1991 | Sheridan | 219/637 |
| 5,473,960 A * | 12/1995 | Sakamoto et al. | 74/422 |
| 6,259,071 B1 * | 7/2001 | Demidovitch et al. | 219/486 |
| 6,954,062 B2 * | 10/2005 | Slates | 324/207.13 |
| 7,112,762 B2 * | 9/2006 | Finley et al. | 219/201 |
| 2002/0017343 A1 * | 2/2002 | Yoshida et al. | 148/328 |
| 2003/0209156 A1 * | 11/2003 | Linnonmaa et al. | 100/327 |
| 2005/0207774 A1 * | 9/2005 | Sone et al. | 399/69 |

* cited by examiner

*Primary Examiner* — Quang T Van
(74) *Attorney, Agent, or Firm* — Filip A. Kowalewski

(57) ABSTRACT

For a shaft of an electric motor with a runout sensing area, an electrical runout value for the runout sensing area is determined, the shaft is rotated and the runout sensing area of the shaft is heated sufficient to reduce the electrical runout value.

21 Claims, 4 Drawing Sheets

SYSTEMS FOR REDUCING SLOW ROLL

CROSS-REFERENCES TO RELATED APPLICATIONS

This application claims priority to and incorporates by reference herein in its entirety, pending U.S. Provisional Patent Application Ser. No. 60/682,075, filed 18 May 2005.

BACKGROUND

Rotating equipment can be utilized in many manufacturing applications. Rotating equipment failures can cause lost production time, injury to personnel, and/or loss of capital equipment. One possible cause of rotating equipment failure can be failures due to excessive vibrations. Accordingly, some rotating equipment can be operated with at least one proximity probe, such as an eddy current proximity probe that can be adapted to continually monitor vibrations (e.g., radial displacements of a rotating part) to detect vibration values in excess of a predetermined threshold.

Proximity probes or proximity measuring systems can be used for the measurement, monitoring, and/or analysis of axial and/or radial shaft vibration (peak-to-peak displacement amplitude) in rotating machinery. A proximity probe or transducer can be placed in a position defined by a mount. Read-outs from proximity probes, such as via oscilloscope, meter, and/or x-y recorder, might not provide an accurate indication of the shaft motion relative to the proximity probe or transducer.

Instead, data provided by the probe can reflect movement of the shaft relative to the probe, electrical properties of the shaft, and/or inaccuracies generated by the probe itself. The impact of shaft movement can be referred to as "mechanical runout". The impact of the electrical properties of the shaft can be referred to as "electrical runout". The impact of the probe's inaccuracies can be referred to as "probe noise".

Eddy current proximity probes can derive distances, such as proximities, utilizing induced electrical currents in the material of the rotating part. Some level of inaccuracy in the values obtained from the probe can be present, however, which can be due to any number of factors, such as instrumentation error, mechanical runout, and/or electrical runout, etc., any of which can vary with measurement location. Electrical runout, often called glitch, can result from variations in electrical properties of the shaft material.

Causes for mechanical runout can comprise aberrations in cross-sectional shape and/or axial flatness, etc., bearing hydrostatic effects, bearing hydrodynamic effects, etc.

A possible test procedure, to assess inaccuracies comprised in values obtained from the probe, can involve rotating a shaft at a speed below and/or far below a normal operating speed. Such a test procedure can be referred to as a "slow roll" test. A displacement signal that a proximity probe provides during a slow roll test can be called a "slow roll value".

Shaft vibrations can be measured by a probe, which can be an inductive sensor. Probes can be configured to measure vibrations caused by a rotation of a shaft. When the shaft is rotating at a relatively slow speed (e.g., less than 250 RPM) a slow roll vibration ("slow roll") can be measured. A portion of slow roll can be due to mechanical defects of the shaft surface and/or defects in the shaft material properties. Slow roll can affect shaft vibration readings. Slow roll can cause a manufactured shaft not to achieve one or more pre-defined manufacturing specifications.

A portion of slow roll can be caused by defects in material properties that can create uneven magnetic properties of the shaft that is read by the probe. Defects can include residual stresses in the shaft material, uneven grain size of the material, mechanical runout of the shaft, and/or shaft magnetism caused by certain non-destructive test methods, etc. In certain exemplary embodiments, proximity transducers can operate in the presence of magnetic field, as long as the field is uniform or symmetrical and not localized to a particular location on the rotor. If different levels of magnetism exist on the shaft surface such that one portion of the surface is highly magnetic while another portion is at a lower magnetic level and/or nonmagnetic, an electrical runout condition can arise. The electrical runout condition can be due to a change in sensitivity on the shaft surface to an applied field from the probe.

Rotating equipment can have a maximum specified slow roll value above which the rotating equipment is considered inoperable since the slow roll can mask shaft movement due to dynamically variable vibration. Hence a system and method to reduce electrical runout in shafts to reduce slow roll is disclosed.

SUMMARY

Certain exemplary embodiments comprise systems, devices, and/or methods for providing a heat treatment procedure to reduce a slow roll value of a proximity probe sensing area of a shaft. In certain exemplary embodiments the heat treatment procedure can improve shaft homogeneity and/or decrease measurement variations in the proximity probe sensing area. Reducing the slow roll value of the sensing area of the shaft can reduce proximity probe sensing errors.

BRIEF DESCRIPTION OF THE DRAWINGS

A wide variety of potential embodiments will be more readily understood through the following detailed description of certain exemplary embodiments, with reference to the accompanying exemplary drawings in which.

DEFINITIONS

Figure 1:
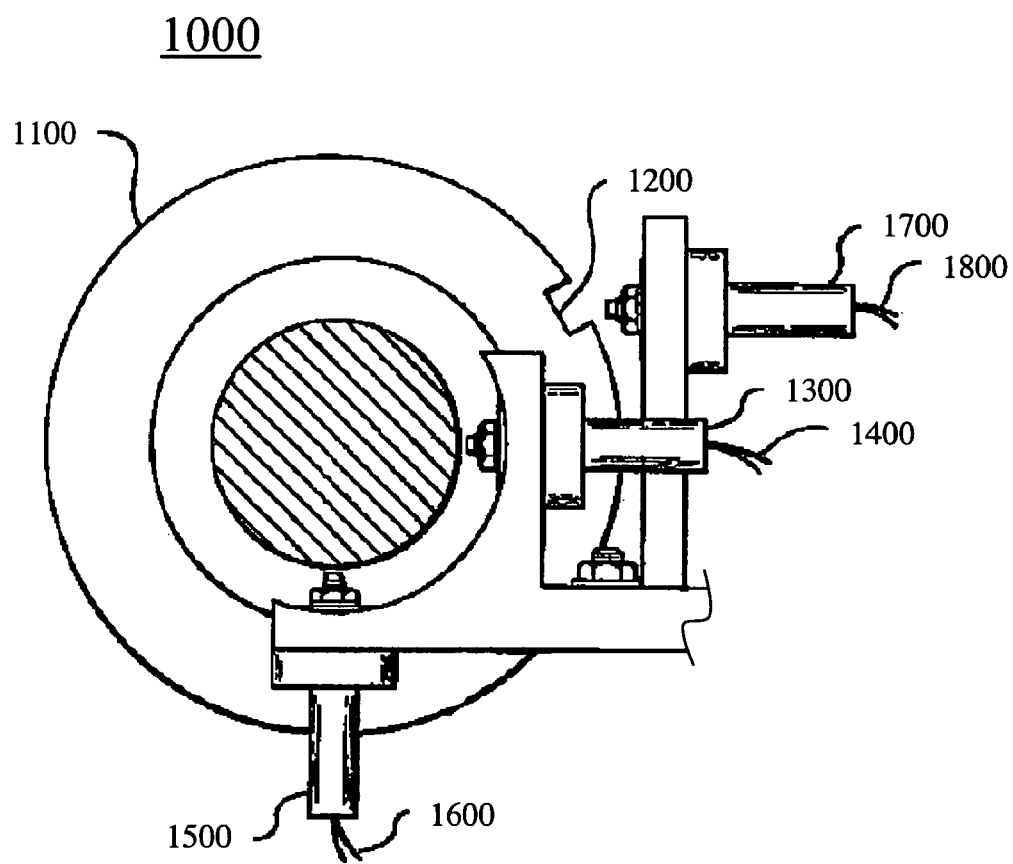
FIG. 1 is a sectional view of a shaft mounted on a system 1000.

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.

activity—an action, act, step, and/or process or portion thereof.

adapted to—made suitable or fit for a specific use or situation.

adapter—a device used to effect operative compatibility between different parts of one or more pieces of an apparatus or system.
adjacent—in close proximity.
air—the earth's atmospheric gas.
and/or—either in conjunction with or in alternative to.
apparatus—an appliance or device for a particular purpose.
apply—to put to use for a purpose.
application—using something for a particular purpose.
approximately—nearly the same as.
area—a surface with determinable boundaries.
associate—to join, connect together, and/or relate.
automatically—acting or operating in a manner essentially independent of external influence or control. For example, an automatic light switch can turn on upon "seeing" a person in its view, without the person manually operating the light switch.
based upon—derived from.
bearing journal—an area of a shaft configured to turn within a device that supports, guides, and reduces the friction of motion between fixed and moving machine parts.
below—less than in magnitude.
calculate—compute.
calibrate—to determine, by measurement or comparison with a standard, a correct value of a reading on a measuring instrument.
can—is capable of, in at least some embodiments.
carbonizing flame—an oxyacetylene flame in which there is an excess of acetylene.
cause—to produce an effect.
comprising—including but not limited to.
configure—to make suitable or fit for a specific use or situation.
configured to—made suitable or fit for a specific use or situation.
connect—to join or fasten together.
control—to direct.
control system—a plurality of electrically conductive devices configured to direct one or more controlled devices.
convert—to transform, adapt, and/or change.
coolant—a first substance configured to reduce thermal energy in a second substance.
cool—to reduce a temperature of a substance.
coupleable—capable of being joined, connected, and/or linked together.
coupling—linking in some fashion.
create—to bring into being.
data—distinct pieces of information, usually formatted in a special or predetermined way and/or organized to express concepts.
data structure—an organization of a collection of data that allows the data to be manipulated effectively and/or a logical relationship among data elements that is designed to support specific data manipulation functions. A data structure can comprise meta data to describe the properties of the data structure. Examples of data structures can include: array, dictionary, graph, hash, heap, linked list, matrix, object, queue, ring, stack, tree, and/or vector.
define—to establish the outline, form, or structure of.
determine—to obtain, calculate, decide, deduce, and/or ascertain.
device—a machine, manufacture, and/or collection thereof.
devoid—lacking.
diameter—a length of a straight line segment passing through a center of an object and terminating at the periphery thereof.
eddy current proximity probe—a device configured to detect changes in a magnetic flux density field generated by the presence of a metal object. Those changes in the field, which are detected by the probe, are proportional to the distance to the object. The probe comprises an inductance element that surrounds a ferrite core which when excited by an electrical current, generates a magnetic flux field. The magnetic field, in turn, generates eddy-currents in the object, thereby causing losses in its flux density. The probe detects those losses in the magnetic flux density.
electrical current—a flow of electrons via a conductor.
electrical frequency—a count of phase cycles of a modulated electrical current and/or voltage during a predetermined time interval.
electric heat—thermal energy generated by the flow of electric charge through a conductor.
electrical induction device—an apparatus configured to provide heat energy, the heat energy resulting from an electric current induced in an object heated by the device.
electric motor—a motion-imparting device powered by electricity.
electrical runout—a property of a rotating shaft causing a proximity probe to give an incorrect indication of a distance between the proximity probe and the rotating shaft.
electrical voltage—an electrical potential.
environment—surrounding conditions.
estimate—to calculate and/or determine approximately and/or tentatively.
exceeding—greater than.
fabricated—made or created.
final—last in a predetermined sequence of events.
final machining—preparing a surface of a mechanical component for use in as a device or a device component.
flood—to provide an abundant flow of a liquid.
focus—to cause energy to concentrate or converge.
generate—to create, produce, give rise to, and/or bring into existence.
greater—larger in magnitude.
ground—shaped or machined utilizing friction.
haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.
heat—(n.) energy associated with the motion of atoms or molecules and capable of being transmitted through solid and fluid media by conduction, through fluid media by convection, and through an empty space and/or fluid by radiation.
heat—(v.) to transfer energy from one substance to another resulting in an increase in temperature of one substance.
heating element—component of a heater or range that transforms fuel or electricity into heat.

indicative—serving to indicate.

indicator—a sign or token.

information—data that has been organized to express concepts.

information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

infrared temperature scanner—a device configured to measure an objects temperature based upon emitted radiation having wavelengths between approximately 750 nanometers and approximately 1 millimeter.

initialize—to prepare something for use and/or some future event.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

install—to connect or set in position and prepare for use.

lathe—a machine for rotating a piece of material, such as wood or metal, about an axis.

length—a measurement of a greatest dimension of an object.

liquid—a state of matter in which as substance exhibits a readiness to flow.

machine—(v.) to cut, shape, or finish via a mechanical device.

machine instructions—directions configured to cause a machine, such as an information device, to perform one or more particular activities, operations, or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine readable medium—a physical structure from which a machine can obtain data and/or information. Examples include a memory, punch cards, etc.

material of construction—a substance used to make an object.

may—is allowed and/or permitted to, in at least some embodiments.

measure—to determine, as a dimension, quantification, and/or capacity, etc. by observation.

mechanical dial indicator—a device configured to measure a mechanical runout of a shaft.

mechanical runout—a property of a rotating shaft indicative of a variation of a distance between the proximity probe and the rotating shaft.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions configured to be executed by processor, such as according to an embodiment disclosed herein.

method—a process, procedure, and/or collection of related activities for accomplishing something.

move—to relocate from a first location to a second location.

movement—a change in place or position.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, Ethernet card, cable modem, digital subscriber line interface, bridge, hub, router, or other similar device.

non-sensing area—a region of a shaft surface not adjacent to an eddy current proximity probe.

obtain—to receive, calculate, determine, or compute.

plurality—the state of being plural and/or more than one.

position—(v.) to locate.

predetermined—established in advance.

prevent—keep an event from happening.

probe—a device comprising a sensor.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

profile—a quantitative description of an object.
project—to calculate, estimate, or predict.
provide—to furnish, supply, give, and/or make available.
range—an extent of variation.
rate—a change of a quantity with respect to time.
reduce—to cause a diminishment in magnitude.
receive—to get as a signal, take, acquire, and/or obtain.
recommend—to suggest, praise, commend, and/or endorse.
regrinding—a second shaping or machining utilizing friction following a first shaping or machining utilizing friction.
reheat—apply heat again following a cooling period.
render—to make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.
repeat—to perform one or more actions again.
repeatedly—again and again; repetitively.
request—to express a desire for and/or ask for.
responsive—reacting to an influence and/or impetus.
revolutions per minute—a number of complete rotations about an axis during a time period of one minute.
rotate—to turn about an axis.
rotation—an act or process of turning around a center or an axis.
select—to make a choice or selection from alternatives.
sensing area—a predetermined region of a shaft surface adjacent to which an eddy current proximity probe will be utilized to measure slow roll of the shaft.
set—a related plurality.
set point—a desired value of a controlled variable.
shaft—a cylindrical bar configured to rotate about an axis.
signal—information, such as machine instructions for activities, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal can be synchronous, asynchronous, hard real-time, soft real-time, non-real time, continuously generated, continuously varying, analog, discretely generated, discretely varying, quantized, digital, continuously measured, and/or discretely measured, etc.
size—physical dimensions, proportions, magnitude, or extent of an object.
slow roll—a sum of instrumentation error, a mechanical runout, and an electrical runout of a rotating shaft.
speed—a linear or rotational velocity.
stator—a stationary portion of a machine.
store—to place, hold, and/or retain data, typically in a memory.
substantially—to a great extent or degree.
supply line—a pipe or tube through which a substance is transferred.
support—to bear the weight of, especially from below.
system—a collection of mechanisms, devices, data, and/or instructions, the collection designed to perform one or more specific functions.
targeted—a desired goal.
temperature—a measure of thermal energy of a substance.
thermal distortion—an undesired change in an object caused by a temperature variation.
threshold—a point that when exceeded produces a given effect or result.
time interval—an amount of time between to specified instants, events, or states.
transmit—to send as a signal, provide, furnish, and/or supply.
user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

value—an assigned or calculated numerical quantity.

via—by way of and/or utilizing.

weight—a value indicative of importance.

DETAILED DESCRIPTION

Certain exemplary embodiments comprise a method comprising a plurality of activities comprising, for a shaft of an electric motor, the shaft comprising a runout sensing area: determining an electrical runout value for the runout sensing area; rotating the shaft; and/or heating the runout sensing area of the shaft sufficient to reduce the electrical runout value.

Certain exemplary embodiments comprise a system comprising: a heating element; and a control system adapted to control a heating of a shaft to a temperature within a predetermined temperature range for a predetermined time interval, the heating sufficient to reduce an electrical runout value of the shaft, the heating can occur while the shaft is rotating.

Certain exemplary embodiments comprise a method comprising a plurality of activities comprising: receiving information indicative of a first runout value for a shaft; automatically determining a temperature range for heating the shaft to reduce the first runout value; and/or automatically determining a time interval for heating the shaft to reduce the first runout value.

Surface heating of predetermined shaft areas can be measured by a probe. The results of surface heating of a shaft can be referred to as a "skin effect". Certain exemplary embodiments can be applied to various shaft sizes. Shafts can be utilized for electric motors, compressors, generator, and/or turbines, etc. For example, electric motors can comprise shafts of a diameter that can be, in inches, approximately 0.5, 1.125, 2.175, 3, 3.25, 5, 6.875, 7, 11.925, 14.375, 24.75, 48, and/or any value or subrange therebetween. Certain exemplary shafts can be used for larger shafts, such as turbine shafts.

Surface heating can treat surface imperfections due to grain size differences and residual stresses to assist in providing a shaft according to one or more specifications. Certain exemplary embodiments can utilize localized heating so that treatment areas receive surface heating while other areas might not. Certain exemplary embodiments can be adjusted for different types of steel and different electrical and magnetic properties. Time and temperature treatment ranges can be adjusted.

Certain exemplary embodiments comprise a method whereby the shaft is positioned horizontally and is supported. For example, the shaft can be supported by two lathe centers within a rotational system or a V block within a fixed system that does not rotate. The electrical induction device can be positioned adjacent (e.g., on, nearly touching, and/or near) the slow roll sensing area prior to treatment. In certain exemplary embodiments, shaft specifications can comprise a location for the slow roll sensing area. The electrical induction device can move axially and/or circumferentially via manual and/or automatic techniques. One or more electrical parameters, such as current, voltage, and/or frequency, as applied by the electrical induction device can be automatically set and/or controlled via the controller. The settings, values, and/or ranges of these electrical parameter setting(s) can be determined from and/or based on a desired heat treatment profile, which can comprise a heat treatment time, temperature, and/or depth from the outer surface of the shaft, and which can be associated with, depend on, and/or be determined from shaft material and/or diameter.

Prior to applying the heating process the shaft can be machined to a diameter that exceeds manufacture specifications. For example, a diameter of a shaft can be machined to a diameter that exceeds specifications by approximately 10 to 15 thousandths of an inch to allow for final surface preparations that might meet one or more customer specifications.

In certain exemplary embodiments, the slow roll sensing area can be heated for approximately one minute. The heating can be to a temperature of approximately 900 F. In certain exemplary embodiments, the shaft can be composed of AISI 4140 steel. After heating the shaft, the shaft can be cooled to a room temperature in an environment with relatively little air movement.

The slow roll sensing area can be machined, ground, and/or burnished to a final specified diameter before, during, and/or after being heat treated. Slow roll can be tested by the probe. If a specified run-out and/or slow roll value is not met, certain exemplary embodiments can repetitively heat and cool the shaft until the specification value is achieved.

FIG. 1 is a sectional view of a shaft 1100 in a system 1000. System 1000 can be adapted to measure a slow roll value and/or an electrical runout value of a sensing area of shaft 1100. Shaft 1100 can be releasably mounted to system 1000, such as by bolting bearings mechanically coupled to shaft 1100 to a frame associated with system 1000. System 1000 can comprise a speed sensor and/or controller adapted to rotate shaft 1100 at a rotational speed sufficiently slow to measure a slow roll value. A rotational speed that is sufficiently slow to measure the slow roll value can be approximately, in revolutions per minute (rpm), 150, 131.3, 104.9, 101, 98.6, 67.4, 45, 33.3, 25, 18.7, 15, 12.9, 9, 6.5, 3.3, 1.2, 0.45, and/or any other value or subrange therebetween.

Shaft 1100 can comprise a sensing area. The sensing area can be associated with proximity probes 1300, 1500, which can be eddy current proximity probes. Proximity probes 1300, 1500 can be probes produced by any proximity probe manufacturer. For example, either of proximity probes 1300, 1500 can be a series 3300 proximity probe or a series 1000 proximity probe manufactured by Bently Nevada of Minden, Nev. Proximity probes 1300, 1500 can be adapted to measure a slow roll value associated with shaft 1100. An electrical runout value associated with the sensing area can be determined from the slow roll value. In certain exemplary embodiments, proximity probe 1300 and/or proximity probe 1500 can be automatically calibrated based upon a material of construction of shaft 1100.

For example, the electrical runout value can be determined by comparing a signal from proximity probe 1300 to a signal from proximity probe 1500 mounted at right angles to each other with respect to shaft 1100, each of which probes can operate and/or be excited at a different frequency. Probe 1300 or probe 1500 can be mounted with an orientation that is substantially the same as a probe adapted to be mounted in a motor comprising shaft 1100. An angular position sensor 1700, such as an angular position sensor manufactured by Bently Nevada of Minden, Nev., can provide a correlation for a signal from each of proximity probes 1300, 1500 to a particular angular location of shaft 1100. For example, angular position sensor 1700 can detect a shaft mark 1200 and can provide timing information indicative of angular displacements of shaft 1100 relative to shaft mark 1200. Signals from proximity probes 1500, 1600 can be provided to an information device communicatively coupled to probes 1300, 1500 by leads 1400, 1600. Signals from angular position sensor 1700 can be provided to the information device communicatively coupled to angular position sensor 1700 via lead 1800. In certain exemplary embodiments, probe 1500 can be a mechanical dial indicator. In such embodiments, a mechanical runout from probe 1500 can be subtracted from a slow roll value obtained from probe 1300 to obtain an electrical runout. The information device can process the signals and provide a slow roll value and/or an electrical runout value associated with the sensing area of shaft 1100.

The information device can be adapted to obtain and/or determine a size, material of construction, and/or location of a sensing area of shaft 1100. The sensing area size can be determined and/or calculated based upon a length and/or diameter of shaft 1100 and/or other characteristics of shaft 1100 and/or proximity probes 1300, 1500.

Figure 2:
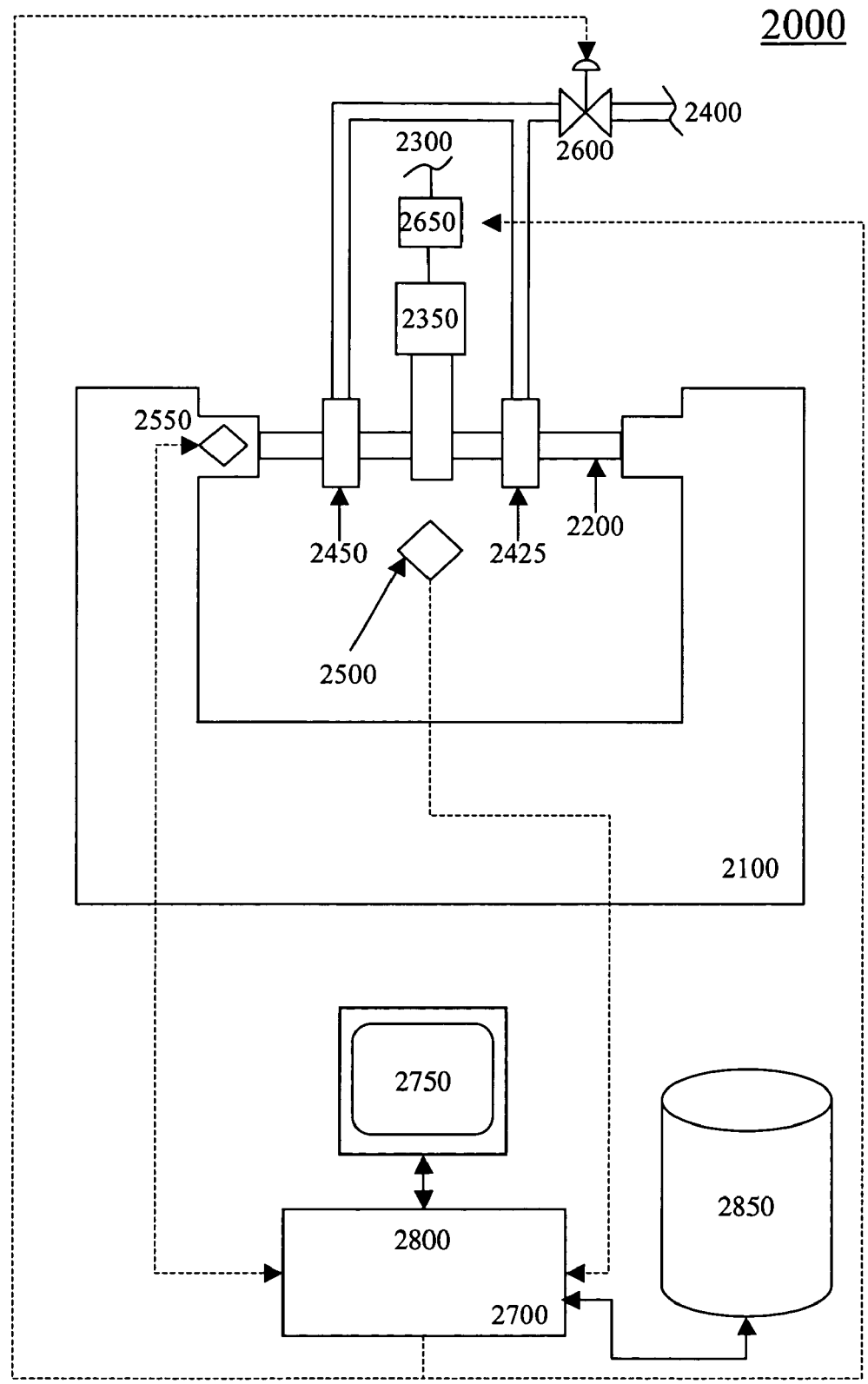
FIG. 2 is a block diagram of an exemplary embodiment of a system 2000.

FIG. 2 is a block diagram of an exemplary embodiment of a system 2000, which can comprise a shaft-holding device 2100. For example, shaft-holding device 2100 can be adapted from a lathe, boring machine, broaching machine, facing machine, grinder, mill, press drill, shaper, tapping machine, and/or threading machine, etc. Shaft-holding device 2100 can comprise steady rests to support a weight of a shaft 2200.

Shaft-holding device 2100 can comprise a speed sensor and/or controller 2550. Speed sensor and/or controller 2550 can be adapted to measure and/or control a rotational speed of shaft 2200 mounted on shaft-holding device 2100. Speed sensor and/or controller 2550 can be adapted to rotate shaft 2200 at approximately a predetermined and/or targeted rotational speed, such as a speed determined appropriate for a process involving heating the shaft to reduce electrical runout.

The targeted rotational speed for heating can be approximately, in rpm, 199, 151.8, 112.1, 107, 95.3, 77.1, 48, 31.8, 18.6, 25, 15, 11.3, 9, 5.4, 3.1, 1.8, 0.76, and/or any other value or subrange therebetween. In certain exemplary embodiments, shaft-holding device 2100 can remain substantially stationary while a slow roll value of shaft 2200 is reduced.

Shaft-holding device 2100 can be adapted to receive shaft 2200. Shaft 2200 can be releasably attached to shaft-holding device 2100 in order to reduce an electrical runout value of shaft 2200. Shaft 2200 can be any shaft from a rotating machine such as a fan, pump, electric motor, gearbox, rotary mixer, centrifuge, and/or agitator, etc. In certain exemplary embodiments, shaft 2200 can be a shaft associated with a new rotating machine. In certain exemplary embodiments, shaft 2200 can be a shaft associated with a previously operated rotating machine.

Shaft 2200 can be comprised of any metal such as an alloy steel. For example, shaft 2200 can be comprised of any alloy steel, such as an alloy steel from series 1000, 4000, 6000, or 9000, etc. For example, shaft 2200 can be comprised of a steel selected from the set of 1045, 4130, 4140, or 4340. In certain exemplary embodiments, shaft 2200 can comprise vacuum degassed steel.

Responsive to a detected electrical runout value associated with shaft 2200 exceeding a predetermined threshold, shaft 2200 can be heated in order to reduce the electrical runout value of the sensing area.

System 2000 can comprise a heating element 2350 that can be adapted to heat shaft 2200 in order to reduce an electrical runout value associated with the sensing area. Heating element 2350 can heat shaft 2200 via electrical induction heating, conductive heating, heating via a neutral flame, heating via a slightly carbonizing flame, and/or heating via a carbonizing flame, etc. A slightly carbonizing flame can be described as comprising a blue envelope and a short bright inner core. In certain exemplary embodiments, when utilizing a flame for heat, the heat can be applied by oscillating the flame. In certain exemplary embodiments, when heating element 2350 utilizes a flame, the flame can be positioned a distance away from shaft 2200, in inches, of approximately 0.5, 0.75, 0.8, 0.9, 1, 1.3, 1.5, 1.6, 1.9, 2, 2.01, 2.4, 3.1, 3.45, 3.6, 4.01, and/or any value or subrange therebetween.

Heating element 2350 can heat shaft 2200 to a temperature and/or temperature range sufficient to reduce the electrical runout value of the sensing area of shaft 2200. For example, system 2100 can be adapted to heat shaft 2200 to a temperature, in degrees Fahrenheit, of approximately 399.9, 487, 522.2, 587.6, 600, 645.5, 699, 703.7, 778.9, 800, 801.1, 850, 922, 1000, 1200, 1321, 1400, and/or any value or subrange therebetween.

Heating element 2350 can apply heat to shaft 2200 for a time interval in minutes of approximately 2.01, 3.9, 4.12, 4.5, 5, 5.7, 6, 6.11, 6.5, 7.2, 7.65, 8, 8.4, 9, 10, 10.3, 11.2, 11.9, 12.5, 15, and/or any value or subrange of time therebetween.

A flow of heat can be regulated and/or controlled via changing a flow of energy from energy source 2300. Energy source 2300 can be a supply of electrical energy, thermal energy, and/or chemical energy (e.g., hydrocarbon based gaseous or liquid fuels). Energy from energy source 2300 can be controlled via regulator 2650. Regulator 2650 can be adapted for automatic and/or manual control of energy from energy source 2300. A design of regulator 2650 can depend upon the nature of energy source 2300. For example, in embodiments utilizing electrical energy, regulator 2650 can be any electrical device adapted to control a flow of electrical current such as a potentiometer, variable R-C circuit, variable inductor, and/or tuning circuit, etc. In embodiments utilizing a gaseous or liquid fuel, regulator 2650 can be a control valve.

In certain exemplary embodiments, where heating element 2350 is an electrical induction device, the flow of heat can be automatically controlled responsive to an automatic determination of a set point for one or more of an electrical current, electrical voltage, and electrical frequency.

A temperature of the sensing area of shaft 2200 can be monitored via an infrared temperature scanner 2500.

While applying heat via heating element 2350, other areas of shaft 2200 can be cooled. For example, collars 2425 and 2450 can be releasably attached to shaft 2200. In certain exemplary embodiments, collars 2425, 2450 can comprise flanges that can be bolted together to releasably attach collars 2425, 2450 to shaft 2200. In certain exemplary embodiments, collars 2425, 2450 can be single piece collars adapted to slidably mount on shaft 2200. A liquid coolant can be supplied to collars 2425, 2450 to cool shaft 2200. For example, the liquid coolant can be applied to areas of shaft 2200 adjacent to the sensing area. The liquid coolant can be any fluid adapted to provide an adequate cooling of shaft 2200, such as water, a glycol based fluid, an oil based fluid, a silicon based fluid, and/or a synthetic aromatic fluid, etc. Applying a liquid coolant to cool shaft 2200 in areas other than the sensing area can resist a thermal distortion of shaft 2200.

A flow of liquid coolant to cool shaft 2200 can be regulated by a control valve 2600. Control valve 2600 can be adapted to adjust a flow of liquid coolant to cool shaft 2200 sufficiently to resist thermal distortion of the shaft, while heating the sensing area of shaft 2200 sufficiently to reduce electrical runout.

After heating, in certain exemplary embodiments, shaft 2200 can be cooled via substantially stationary ambient air. In certain exemplary embodiments, shaft 2200 can be convectively cooled via discernibly moving air currents.

In certain exemplary embodiments, system 2000 can comprise a control system comprising an information device 2700, which can comprise a client program 2800 and a user interface 2750. Information device 2700 can receive information regarding shaft 2200 via sensors and/or inputs received from a user. Information regarding shaft 2200 can comprise a metallurgical composition, length, diameter, profile, electrical runout value prior to heat treatment and/or maximum desired electrical runout value, etc.

Client program 2800 can be adapted to determine the sensing area, which can vary depending on the type of probe used, the shaft diameter, shaft material, machine design, bearing location, etc.

Client program 2800 can be adapted to determine the temperature range and/or the time interval for heating shaft 2200 to reduce electrical runout. The temperature range can be determined based upon shaft metallurgy, an electrical runout value, a targeted threshold for reducing the electrical runout value, and/or other characteristics of shaft 2200, etc. A maximum temperature for heating shaft 2200 can be determined from shaft metallurgy. The maximum temperature can be determined in order to resist substantially impairing physical properties of shaft 2200 as a result of grain structure changes.

Information related to and/or obtained by client program 2800 can be processed and/or stored. For example, a database can be stored in a memory device 2850, which can be comprised by, and/or communicatively coupled to, information device 2700. Information device 2700 can store and/or process information related to metallurgical alloys such as time-temperature transformation curves associated with particular metallurgical alloys.

Client program 2800 can be adapted to determine an electrical parameter, such as an electrical current, electrical voltage, and/or electrical frequency to be supplied to an electrical induction device configured to heat shaft 2200 to the predetermined electrical parameter(s), such as temperature, time, and/or shaft depth. The electrical parameter(s) can be automatically determined based upon a material of construction and/or one or more dimensions of shaft 2200. In certain exemplary embodiments, client program 2220 can be configured to control the electrical parameter within a predetermined range. The predetermined range can be verified and/or adjusted via one or more readings from infrared temperature scanner 2500.

The range of time durations and/or periods for heating shaft 2200 can be determined based upon metallurgical properties, dimensions, and/or other characteristics of shaft 2200. The range of heating time durations can be related to the temperature range in that the heating time can be selected to resist substantially impairing physical properties of shaft 2200 as a result of grain structure changes. Thus, at a higher temperature range for heating shaft 2200, the heating time duration might be reduced as compared a different time duration associated with a lower temperature range.

Client program 2800 can be adapted to control regulator 2650 responsive to a temperature and/or or a rate of change of temperature measured by infrared temperature scanner 2500. Controlling regulator 2650 can control the temperature of the slow roll sensing area within a temperature range for a period of time within a range of time periods.

In certain exemplary embodiments, client program 2800 can be adapted to determine a targeted rotational speed for machine 2100. The targeted rotational speed can be determined based upon characteristics of shaft 2200.

Client program 2800 can be adapted to determine a cooling rate for the slow roll sensing area of the shaft. The cooling rate can be determined based upon metallurgy and/or other characteristics of shaft 2200. In certain exemplary embodiments, energy flow from heating element 2350 can be reduced gradually to achieve a targeted cooling rate.

Client program 2800 can be adapted to control liquid coolant flow to shaft 2200, via adjusting control valve 2600, responsive to a flow of heat to heating element 2350 and/or information obtained by infrared temperature scanner 2500.

In certain exemplary embodiments, client program 2800 can be adapted to adaptively learn and improve performance of system 2000. For example, client program 2800 can receive electrical runout measurements before and/or after a heat treatment of shaft 2200 and/or can receive information related to material and/or strength properties of shaft 2200. Client program 2800 can be adapted to correlate variables measured during heat treatment to objective results regarding electrical runout and/or shaft strength properties. Client program 2800 can be adapted to randomly and/or heuristically vary parameters associated with heat treatment such as the temperature range, time interval, electrical parameters, and/or flow of liquid coolant. Client program 2800 can use an optimization algorithm to seek optimal points on response surfaces associated with heat treatment to reduce electrical runout in shafts. For example, the optimization algorithm can use a linear programming technique, golden search algorithm, Hooke and Jeeves' method, and/or Nelder and Mead's method, etc.

User interface 2750 can be adapted to render information regarding reducing the electrical runout value of shaft 2200. For example, user interface 2750 can render information regarding a detected slow roll value or an electrical runout measurement. User interface 2750 can render information regarding heating shaft 2200, such as a temperature detected by infrared temperature scanner 2500, a flow of heat to heating element 2350, and/or a liquid coolant flow to collars 2425, 2450. User interface 2750 can be adapted to render information regarding the heating profile, temperature range, and/or the time interval.

Memory device 2850 can be a machine-readable medium comprising machine instructions for performing one or more activities. Information device 2700 can be communicatively coupled to a network (not illustrated) and/or a plurality of information devices (not illustrated). Information device 2700 can transmit or receive a signal comprising machine instructions related to controlling a heating and/or electrical runout reduction of shaft 2200.

Figure 3:
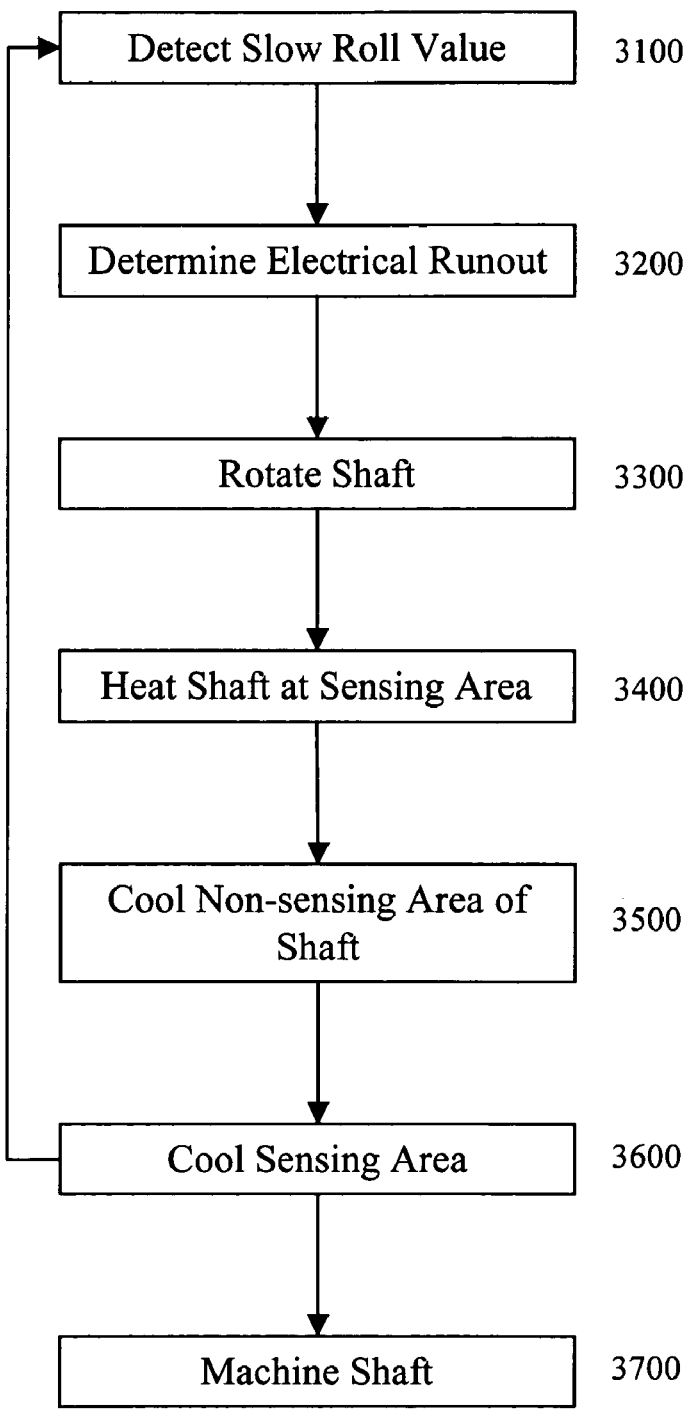
FIG. 3 is a flowchart of an exemplary embodiment of a method 3000.

FIG. 3 is a flowchart of an exemplary embodiment of a method 3000. In certain exemplary embodiments, a shaft can be machined to a diameter greater than a final shaft diameter prior to measuring a slow roll value. A material of construction of the shaft, a length of the shaft, and/or a diameter of the shaft can be obtained. At activity 3100, a slow roll value associated with a sensing area can be measured, detected, and/or received. The sensing area can be a slow roll sensing area and/or a runout sensing area of a shaft. In certain exemplary embodiments, the shaft can be a shaft of an electric motor. The slow roll value and/or an electrical runout can be detected via one or more probes, such as an eddy current proximity probe and/or a mechanical dial indicator. The mechanical dial indicator and/or the probe can be positioned in the slow roll sensing area and can be configured to measure mechanical runout. In certain exemplary embodiments, one or more probes can be automatically calibrated based upon a material of construction of the shaft.

In certain exemplary embodiments, the slow roll value can be compared to a predetermined threshold. If the slow roll value is below the predetermined threshold, the shaft can be utilized without reducing the slow roll value. If the slow roll value exceeds a predetermined threshold, activities can continue at activity 3200.

At activity 3200, an electrical runout value associated with the sensing area can be determined. The electrical runout value can be determined based upon the slow roll value and information indicative of a mechanical runout associated with the slow roll value. In certain exemplary embodiments, the electrical runout value can be compared to a predetermined threshold. If the electrical runout value is below the predetermined threshold, the shaft can be utilized without reducing the electrical runout value. If the electrical runout value exceeds a predetermined threshold, activities can continue at activity 3300.

At activity 3300, the shaft can be rotated. In certain exemplary embodiments, the shaft can be rotated at a speed of less than approximately 30 revolutions per minute in order to heat the sensing area to reduce the electrical runout value of the shaft.

At activity 3400, the shaft can be heated at the sensing area. The sensing area of the shaft can be heated to approximately within a predetermined temperature range for approximately a predetermined time interval, the heating of the shaft can be sufficient to reduce the electrical runout value. In certain exemplary embodiments, a fire extinguisher can be provided for safety purposes. In certain exemplary embodiments, the heat can be provided by an electrical induction device. The electrical induction device can be automatically controlled responsive to an automatic determination of a set point for one or more of an electrical current, electrical voltage, and electrical frequency.

At activity 3500, a non-sensing area of the shaft can be cooled via a liquid coolant. Cooling the non-sensing area of the shaft can resist a thermal distortion of the non-sensing area. For example, a coolant line can be positioned on a bearing journal area of the shaft, which can flood the bearing journal area with a liquid coolant during heating activity 3400. Certain exemplary embodiments can comprise water/coolant hoses and/or a sump truck for providing liquid coolant.

At activity 3600, the sensing area can be cooled. In certain exemplary embodiments, the shaft can be air cooled, at a controlled or uncontrolled rate, such as to a temperature of less than approximately 200 degrees Fahrenheit.

Activity 3100 through activity 3600 can be repeated until a measured electrical runout value and/or slow roll value is less than a predetermined threshold.

At activity 3700, the shaft can be ground and/or machined. In certain exemplary embodiments, sensing surfaces of the shaft can be ground to within approximately five thousandths of an inch of a final radius prior to heating the shaft for reducing electrical runout. Grinding and/or machining the shaft can prepare the shaft for use in a machine such as an electric motor.

Figure 4:
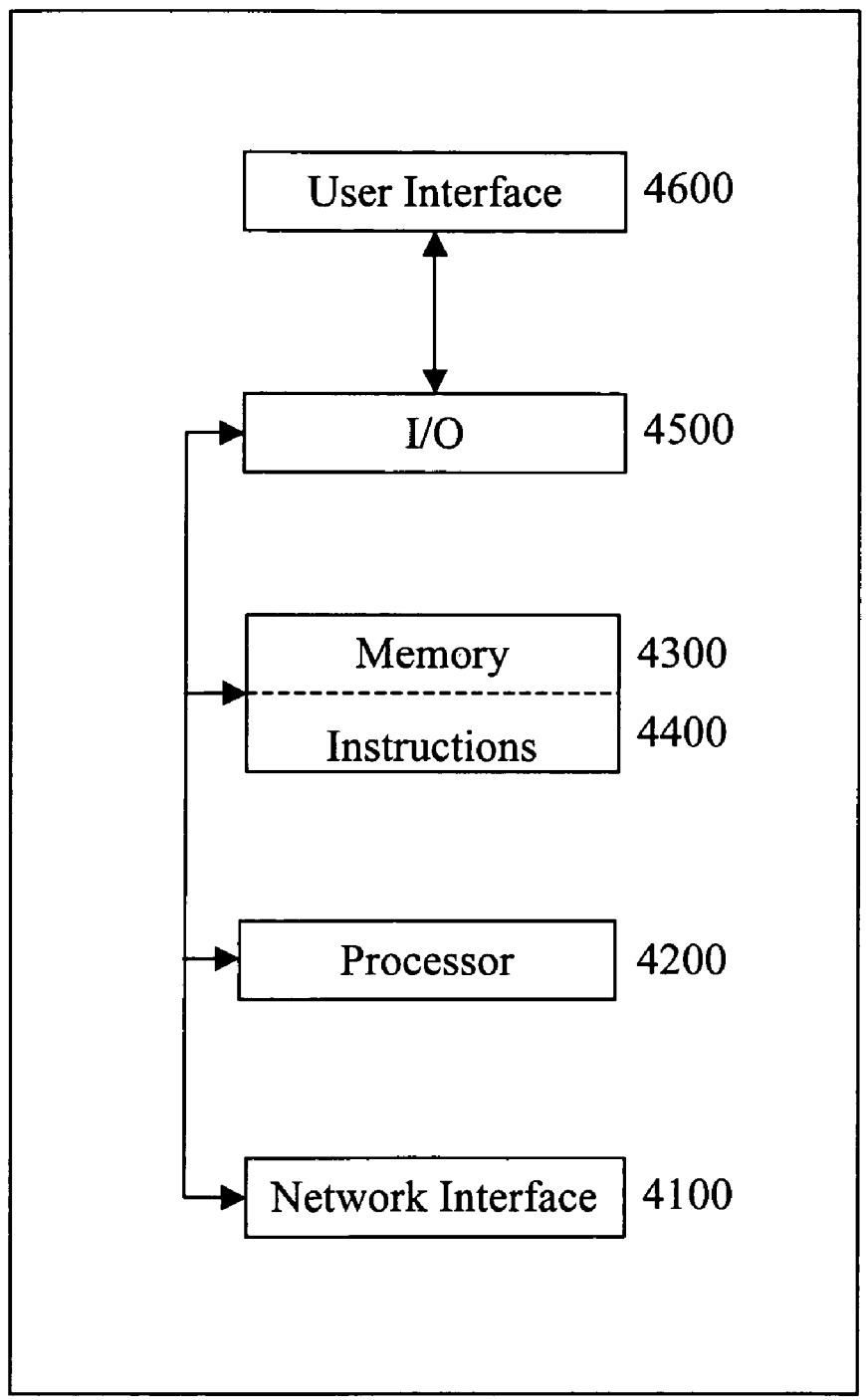
FIG. 4 is a block diagram of an exemplary embodiment of an information device 4000.

FIG. 4 is a block diagram of an exemplary embodiment of an information device 4000, which in certain operative embodiments can comprise, for example, information device 2700 of FIG. 2. Information device 4000 can comprise any of numerous components, such as for example, one or more network interfaces 4100, one or more processors 4200, one or more memories 4300 containing instructions 4400, one or more input/output (I/O) devices 4500, and/or one or more user interfaces 4600 coupled to I/O device 4500, etc.

In certain exemplary embodiments, via one or more user interfaces 4600, such as a graphical user interface, a user can view a rendering of information related to heating a shaft to reduce electrical runout of a shaft.

Note

Still other practical and useful embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application.

Thus, regardless of the content of any portion (e.g., title, field, background, summary, abstract, drawing figure, etc.) of this application, unless clearly specified to the contrary, such as via an explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

any elements can be integrated, segregated, and/or duplicated;

any activity can be repeated, performed by multiple entities, and/or performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

Accordingly, the descriptions and drawings are to be regarded as illustrative in nature, and not as restrictive.

What is claimed is:

1. A system for controlling shaft heating, comprising:
an electrical induction device;
a probe automatically calibrated based upon a material of construction of a shaft of an electric motor; and
a control system configured to:
control an application of heat from said electrical induction device to a slow roll sensing area of said shaft for a predetermined time interval, said application of heat sufficient to reduce an electrical runout associated with a measured first slow roll value, said first slow roll value determined based on one or more measurements obtained from said probe, said heat applied according to a heat treatment profile, said heat treatment profile comprising said predetermined time interval, a predetermined temperature, and a predetermined depth from an outer surface of said shaft;

measure a first slow roll value in said slow roll sensing area with said probe;

permanently alter a grain structure of said shaft by said application of heat based on said first slow roll value; and control said application of heat to said slow roll sensing area automatically responsive to an automatic determination of a set point for one or more of an electrical current, electrical voltage, and electrical frequency.

2. The system of claim 1 wherein the probe is an eddy current proximity probe system configured to measure said first slow roll value.

3. The system of claim 1, further comprising:
a device configured to rotate said shaft at a predetermined rotational speed.

4. The system of claim 1, further comprising:
an infrared temperature scanner configured to measure a temperature associated with said slow roll sensing area.

5. The system of claim 1, wherein said control system is configured to obtain a diameter of said shaft, said set point determined based upon said diameter of said shaft.

6. The system of claim 1, wherein said control system is configured to obtain a diameter of said shaft.

7. The system of claim 1, wherein said control system is configured to obtain a mechanical runout of said shaft with a mechanical dial indicator, said electrical runout determined based upon a said first slow roll value minus said mechanical runout.

8. The system of claim 1, wherein said control system is configured to obtain said material of construction of said shaft.

9. The system of claim 1, wherein said control system is configured to calibrate said probe based upon said material of construction of said shaft.

10. The system of claim 1, wherein said control system is configured to determine said sensing area of said shaft.

11. The system of claim 1, wherein said control system is configured to receive a measured second slow roll value after said application of heat.

12. The system of claim 1, wherein said control system is configured to:
receive a measured second slow roll value after said application of heat; and
reheat said slow roll sensing area responsive to a determination that said second slow roll value is above a predetermined threshold.

13. The system of claim 1, wherein said control system is configured to receive said measured first slow roll value.

14. The system of claim 1, wherein said system is configured to reduce said electrical runout value in said slow roll sensing area.

15. The system of claim 1, wherein said control system is configured to monitor a temperature of said sensing area via an infrared temperature scanner.

16. The system of claim 1, wherein said system is configured to cool said shaft in air.

17. The system of claim 1 wherein the control system is further configured to:
control an application of coolant to said slow roll sensing area.

18. The system of claim 1 wherein the control system is further configured to:
control an application of coolant to a non-sensing area adjacent said slow roll sensing area of said shaft.

19. The system of claim 18 further comprising:
one or more collars releasably attached to said shaft; and
wherein the control system is further configured to control said application of coolant to said one or more collars.

20. A system for controlling shaft heating, comprising:
an electrical induction device;
a temperature measurement device;
a probe automatically calibrated based upon a material of construction of a shaft; and
a control system configured to:
control an application of heat from said electrical induction device to a slow roll sensing area of said shaft for a predetermined time interval, said application of heat sufficient to reduce an electrical runout associated with a measured slow roll value, said slow roll value determined based on one or more measurements obtained from said probe, said heat applied according to a heat treatment profile, said heat treatment profile comprising said predetermined time interval, a predetermined temperature, and a predetermined depth from an outer surface of said shaft;
measure a first slow roll value in said slow roll sensing area with said probe;
permanently alter a grain structure of said shaft by said application of heat based on said first slow roll value; and
automatically control said application of heat to said slow roll sensing area responsive to an automatic determination of a set point for one or more of an electrical current, electrical voltage, and electrical frequency.

21. A system for controlling shaft heating, comprising:
a probe automatically calibrated based upon a material of construction of a shaft; and
a control system configured to:
control an application of heat from said electrical induction device to a slow roll sensing area of said shaft for a predetermined time interval, said application of heat sufficient to reduce an electrical runout associated with a measured slow roll value, said slow roll value determined based on one or more measurements obtained from said probe, said heat applied according to a heat treatment profile, said heat treatment profile comprising said predetermined time interval, a predetermined temperature, and a predetermined depth from an outer surface of said shaft;
measure a first slow roll value in said slow roll sensing area with said probe;
permanently alter a grain structure of said shaft by said application of heat based on said first slow roll value; and
automatically control said application of heat to said slow roll sensing area responsive to an automatic determination of a set point for one or more of an electrical current, electrical voltage, and electrical frequency.

* * * * *